United States Patent [19]

Seidman et al.

[11] Patent Number: 5,429,923
[45] Date of Patent: Jul. 4, 1995

[54] METHOD FOR DETECTING HYPERTROPHIC CARDIOMYOPHATHY ASSOCIATED MUTATIONS

[75] Inventors: Christine Seidman; John Seidman, both of Milton; Hugh Watkins, Brookline; Anthony Rosenzweig, Newton, all of Mass.

[73] Assignees: President and Fellows of Harvard College, Cambridge; Brigham and Women's Hospital; The General Hospital, both of Boston, all of Mass.

[21] Appl. No.: 989,160

[22] Filed: Dec. 11, 1992

[51] Int. Cl.$^6$ .......................... C12Q 1/70; C12P 19/34; C07H 17/00
[52] U.S. Cl. .......................................... 435/6; 435/91.1; 536/23.1; 536/24.3; 536/24.33; 935/2; 935/84
[58] Field of Search ........................ 435/6, 91, 91.1; 536/18.7, 23.1, 24.3, 24.33; 935/2, 84

[56] References Cited

U.S. PATENT DOCUMENTS 4,683,195  7/1987  Mullis et al. .......................... 435/6

OTHER PUBLICATIONS

Jaenieke et al. Genomics 8:194 (1990).
Saiki et al. Science 230:1350.
S. E. Antonarakis, "Diagnosis of Genetic Disorders at the DNA Level", *The New England Journal of Medicine*, vol. 320, No. 3.
R. Myers et al., "Detection of Single Base Substitutions by Ribonuclease Cleavage at Mismatches in RNA:DNA Duplexes", *Science*, vol. 230, Dec. 13, 1985.
A. Rosenzweig et al., "Preclinical Diagnosis of Familial Hypertrophic Cardiomyopathy by Genetic Analysis of Blood Lymphocytes", *New England Journal of Medicine*, 325:1753–1760 (Dec. 19, 1991).
J. A. Jarcho et al., "Mapping a Gene for Familial Hypertrophic Cardiomyopathy to Chromosome 14q1", *New England Journal of Medicine*, 321:1372–1378 (Nov. 16, 1989).
S. D. Solomon et al., "Familial Hypertrophic Cardiomyopathy is a Genetically Heterogeneous Disease" *J. Clinic. Invest.*, vol. 86, Sep. 1990, 993–999.
G. Tanigawa et al., "A Molecular Basis for Familial Hypertrophic Cardiomyopathy: An $\alpha/\beta$ Cardiac Myosin Heavy Chain Hybrid Gene", *Cell*, vol. 62, 991–998, Sep. 7, 1990.
Geisterfer-Lowrance et al., "A Molecular Basis for Familial Hypertrophic Cardiomyopathy: A $\beta$ Cardiac Myosin Heavy Chain Gene Missense Mutation", *Cell*, vol. 62, 999–1006, Sep. 7, 1990.
Seidman et al., "Mutations in Cardiac Myosin Heavy Chain Genes Cause Familial Hypertrophic Cardiomyopathy," *Mol. Biol. Med.*, vol. 8, 159–166 (1991).

(List continued on next page.)

*Primary Examiner*—Margaret Parr
*Assistant Examiner*—Miguel H. Escallon
*Attorney, Agent, or Firm*—Lahive & Cockfield

[57] ABSTRACT

A method is described for diagnosing individuals as having hypertrophic cardiomyopathy, e.g. familial or sporadic hypertrophic cardiomyopathy. The method provides a useful diagnostic tool which becomes particularly important when testing asymptomatic individuals suspected of having the disease. Symptomatic individuals have a much better chance of being diagnosed properly by a physician. Asymptomatic individuals from families having a history of familial hypertrophic cardiomyopathy may be selectively screened using the method of this invention allowing for a diagnosis prior to the appearance of any symptoms. Individuals having the mutation responsible for the disease may be counseled to take steps which hopefully would prolong their life, i.e. avoid rigorous exercise. The methodology used in the above method also has broad applicability and may be used to detect other disease-associated mutations in DNA obtained from subjects being tested for other disease-associated mutations.

5 Claims, 7 Drawing Sheets

OTHER PUBLICATIONS

Watkins et al., "Characteristics and Prognosis Implications of Myosin Missense Mutations in Familial Hypertrophic Cardiomyopathy", *New England Journal of Medicine,* 326:1108–1114 (Apr. 23, 1992).

R. G. Cotton, "Detection of Singl Base Changes in Nucleic Acids", *Biochem J.,* 263:1–10 (1989).

Roberts et al., "Direct Diagnosis of Carriers of Duchenne and Becker Muscular Dystrophy by Amplification of Lymphocyte RNA", *The Lancet,* vol. 336, 1523–1526, Dec. 22/29, 1990.

J. Chelly et al., "Transcription of the Dystrophin Gene in Human Muscle and Non-Muscle Tissues" *Nature,* vol. 333, 858–860, 30 Jun. 1988.

Epstein et al., "Differences in Clinical Expression of Hypertrophic Cardiomyopathy Associated With Two Distinct Mutations in the β-Myosin Heavy Chain Gene", *Circulation,* vol. 86, No. 2, Aug. 1992.

Maron et al., "Patterns and Significance of Distribution of Left Ventricular Hypertrophy in Hypertrophic Cardiomyopathy", *The American Journal of Cardiology,* vol. 48, 418–428, Sep. 1981.

McKenna et al., "Echocardiographic Measurement of Right Ventricular Wall Thickness in Hypertrophic Cardiomyopathy: Relation to Clinical and Prognostic Features", *JACC* vol. 11, No. 2 351-8, Feb. 1988.

L. Shapiro and W. McKenna, "distribution of Left Ventricular Hypertrophy in Hypertrophic Cardiomyopathy: A Two Dimensional Echocardiographic Study", *JACC* vol. 2, No. 3, 437–444, Sep. 1983.

G. Sarkar and S. Sommer, "Access to a Messenger RNA Sequence or its Protein Product Is Not Limited by Tissue or Species Specificity", *Science,* vol. 244, 331–334, Apr. 21, 1989.

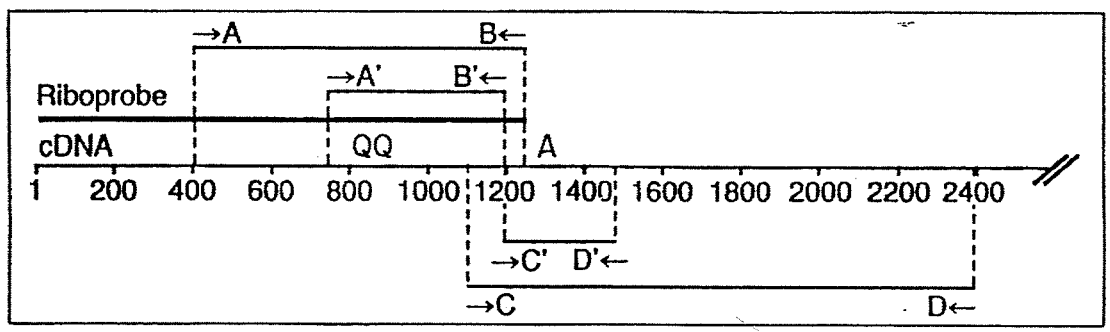
FIG. IA
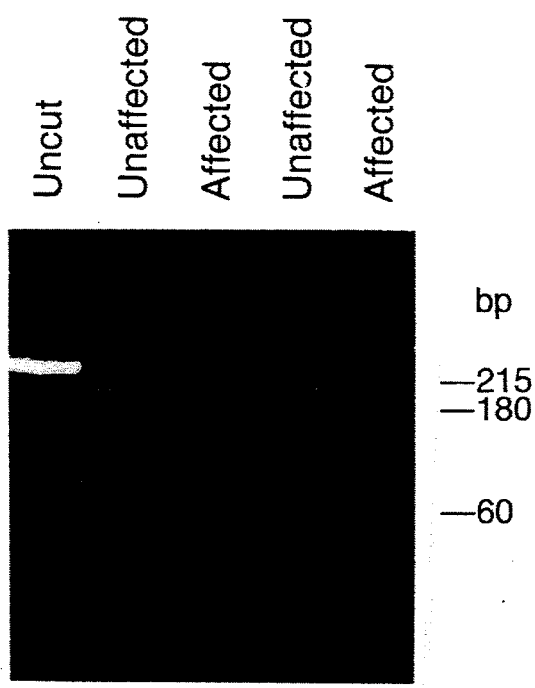
FIG. IB

FIG. 4A
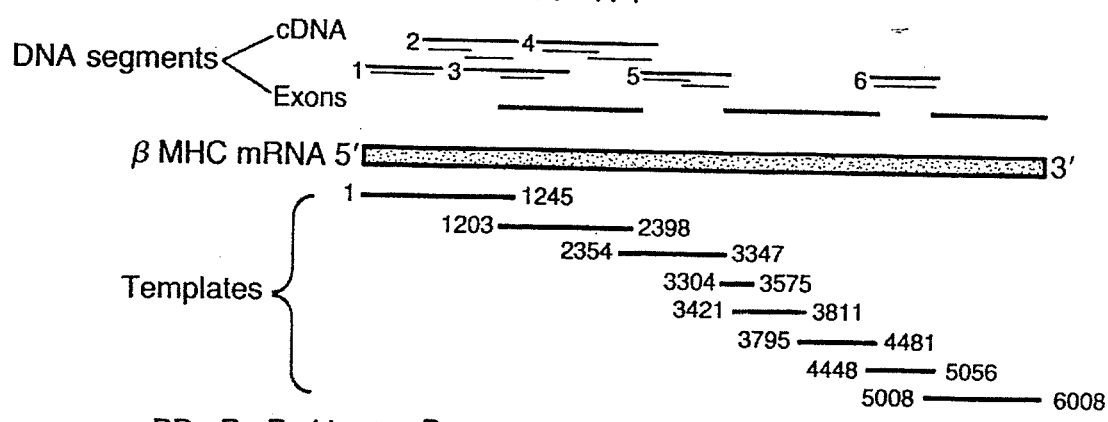
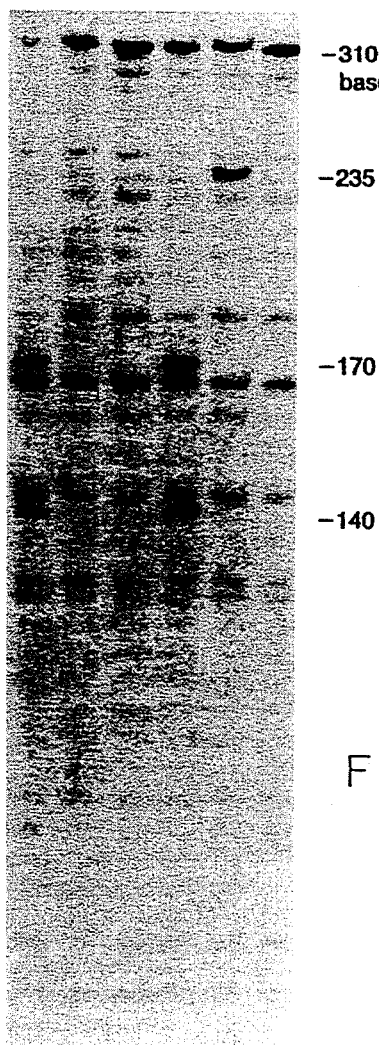
FIG. 4B

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CAAGGATCGC TACGGCTCCT GGAT    24

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCGGATCCAG GTAGGCAGAC TTGTCAGCCT    30

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:3:

ATGCCAACCC TGCTCTGGAG GCCT 24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:4:

CTTCATGTTT CCAAAGTGCA TGAT 24

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:5:

CTGGGCTTCA CTTCAGAGGA GAAAA 25

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:6:

GCGGTACCCC AGCAGCCCGG CCTTGAAGAA 30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:7:

GGGAATTCGC GGAGCCAGAC GGCACTGAAG 30

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:8:

CCCTCCTTCT TGTACTCCTC CTGCTC 26

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CAACTCATCA CCACTCTCTT CCATC    25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GCTGAGCCTA GCAGATTCAT GGCAC    25

METHOD FOR DETECTING HYPERTROPHIC CARDIOMYOPHATHY ASSOCIATED MUTATIONS

GOVERNMENT FUNDING

Work described herein was supported under grants (HL 46320, HI 41474, and HL 42467) awarded by the National Institutes of Health. The U.S. government therefore may have certain rights to this invention.

BACKGROUND

The use of an individual's genetic information in the diagnosis of a disease is becoming more prevalent. Many diseases are caused by a defect in a single gene of an individual. All known autosomal dominant, autosomal recessive and X-linked disorders are believed to be caused by a defect in a single gene (Antonarakis, *New England Journal of Medicine* Vol. 320, No. 3:153-63 (1981)). Genes responsible for some diseases or disorders have been cloned and characterized. The defect in the gene may be a gross gene alteration, a small gene alteration or even a point mutation. Examples of some diseases caused by a mutation in a gene include Gaucher's disease, hemophelia A and B, Duchenne's muscular dystrophy, sickle cell anemia, Tay-Sachs disease, phenylketonoria and cystic fibrosis.

Familial hypertrophic cardiomyopathy (hereinafter FHC) has been linked to mutations in the $\beta$ cardiac myosin heavy-chain gene (Tanigawa et al., Cell 62:991-998 (1990)); Geisterfer-Lowrance et al., Cell 61:999-1006 (1990)). Tanigawa et al. studied a single family (Family B) and hypothesized that the FHC in this family was due to a mutation that results in the formation of an $\alpha/\beta$ cardiac myosin heavy-chain hybrid gene. Geisterfer-Lowrance et al. also studied a single family and hypothesized that a missense mutation in the $\beta$ cardiac myosin heavy-chain gene caused FHC in the family studied.

FHC is a well characterized autosomal dominant disorder or disease. It is autosomal dominant in that fifty percent of the children of affected parents eventually become afflicted with the disease. FHC is characterized by unexplained myocardial hypertrophy. The clinical symptoms of individuals having FHC are variable and some individuals do not have any symptoms. The symptoms of FHC include dypsnea, angina, ischemia. Pathological findings of the disease include increased myocardial mass with myocyte and myofibrillar disarray.

Presently, the diagnosis of individuals having FHC relies on the presence of typical clinical symptoms and the demonstration of unexplained ventricular hypertrophy. Sudden, unexpected death is the most serious consequence of FHC. Sudden death occurs in both symptomatic and asymptomatic individuals and FHC has an annual mortality of approximately four percent from sudden death.

SUMMARY OF THE INVENTION

The present invention provides a method for diagnosing individuals as having hypertrophic cardiomyopathy (hereinafter HC), e.g. familial or sporadic hypertrophic cardiomyopathy (hereinafter FHC or SHC). The method provides a useful diagnostic tool which becomes particularly important when screening asymptomatic individuals suspected of having the disease. Symptomatic individuals have a much better chance of being diagnosed properly by a physician. Asymptomatic individuals from families having a history of FHC may be selectively screened using the method of this invention allowing for a diagnosis prior to the appearance of any symptoms. Individuals having the mutation responsible for FHC may be counseled to take steps which hopefully would prolong their life, i.e. avoid rigorous exercise.

A method involving both an amplification and detecting step for detecting mutations associated with hypertrophic cardiomyopathy has not been previously described. The present method for detecting the presence or absence of a mutation associated with hypertrophic cardiomyopathy involves amplifying $\beta$ cardiac myosin heavy-chain DNA forming an amplified product and detecting the presence or absence of a mutation associated with hypertrophic cardiomyopathy in the amplified product.

The present invention further pertains to a method for diagnosing familial hypertrophic cardiomyopathy. Prior to the present invention, there were no extensive studies involving a large number of families which established that this disease or disorder was caused by point mutations in the $\beta$ cardiac myosin heavy-chain gene when the causative mutation is located within this gene. The process of diagnosing a disease caused by a point mutation is considerably more complex if multiple genes and multiple point mutations are responsible for the particular disease. FHC falls into this complex category because it is due to defects in the $\beta$ cardiac myosin heavy-chain gene in approximately 50% of the families and unrelated families have different disease-causing point mutations. The present invention is based, at least in part, on the discovery that FHC is caused by point mutations when the mutation involves the $\beta$ cardiac myosin heavy-chain gene and even further that different unrelated families have different disease-causing point mutations. The large size of the gene makes identifying disease-causing mutations laborious. The present invention provides a relatively rapid and easy method for accomplishing this difficult task.

The method for diagnosing FHC includes obtaining a sample of $\beta$ cardiac myosin heavy-chain DNA derived from the subject being screened for FHC and diagnosing the subject for FHC by detecting the presence or absence of a FHC-causing mutation in the $\beta$ cardiac myosin heavy-chain DNA as an indication of the disease. The $\beta$ cardiac myosin heavy-chain DNA may be cDNA reverse transcribed from RNA obtained from the subject's blood lymphocytes.

The present invention also provides a non-invasive method for diagnosing HC that exploits the ectopic expression of this gene in nucleated blood cells, e.g., peripheral-blood mononuclear cells, allowing for access to $\beta$ cardiac myosin heavy-chain transcripts from peripheral blood. Access to $\beta$ cardiac myosin heavy-chain transcripts in peripheral blood permits efficient amplification of coding sequences which can be analyzed for small deletions, alternative splicing or point mutations with RNase protection assays. The non-invasive method for diagnosing HC involves obtaining a blood sample from a subject being screened for HC and isolating $\beta$ cardiac myosin heavy-chain RNA from the blood sample. The subject is diagnosed for HC by detecting the presence or absence of an HC-associated mutation in the RNA as an indication of the subject having the disease. Mutations in the RNA may be detected by reverse transcribing the RNA into cDNA and subsequently detecting HC-associated mutations in the cDNA.

The present invention further provides a method that allows the detection of disease-causing mutations in a DNA sequence associated with a disease. Screening for a mutation in a person at risk for a particular disease can be accomplished rapidly and relatively easily through the presently described method. The method of this invention may be used to detect mutations responsible for diseases or disorders such as hypertrophic cardiomyopathy, e.g. familial or sporadic, cystic fibrosis, Gaucher's disease, hemophilia A and B, Duchenne's muscular dystrophy, sickle cell anemia, Tay-Sachs disease, and phenylketonuria.

The method for detecting the presence or absence of a disease-associated mutation in a DNA sequence involves amplifying a DNA sequence suspected of containing a disease-associated mutation forming an amplified product, combining the amplified product with an RNA probe completely hybridizable to a normal DNA sequence associated with the disease forming a hybrid double strand having an RNA and DNA strand. Subsequently, the hybrid double strand is contacted with an agent capable of digesting an unhybridized portion of the RNA strand and the presence or absence of an unhybridized portion of the RNA strand is detected as an indication of the presence or absence of a disease-associated mutation in the corresponding portion of the DNA strand. The method of this invention may be used to detect mutations which are reflected in the RNA. The method may be used to detect mutations of a size which is less than or equal to the amplified piece of DNA defined by the primers. Preferably, the mutation is less than about 500 bp, more preferably less than about 100 bp, even more preferably less than about 10 bp, and most preferably a point mutation, i.e. a change in a single nucleotide.

Other aspects of this invention pertain to kits including containers holding reagents used in the above-described methods and a method for determining the estimated life expectancy of a person having FHC using the above-described methods. The components of the kit also are part of this invention. These aspects are described in more detail below.

BRIEF DESCRIPTION OF THE DRAWINGS

FIG. 1A shows the nested polymerase chain reaction (hereinafter PCR) used to amplify a β cardiac myosin heavy-chain complementary DNA (cDNA) with nucleotide residues indicated by numbers. Reverse transcriptase was used to obtain the cDNA from mRNA extracted from peripheral-blood mononuclear cells or cell lines transformed by Epstein-Barr virus. The cDNA was used as a template for the initial PCR with primers A and B or C and D. The resulting products were diluted 1:1000, and PCR was repeated with internal primers A' and B' or C' and D'. The positions of the missense mutations found in the previously described Family A (residue 1294) and in presently described Family QQ (residue 832) are indicated. The cDNA fragment used as the template for the riboprobe used in RNase protection assays (shown in FIG. 2) is also indicated.

FIG. 1B is a photograph showing the normal and mutant β cardiac myosin heavy-chain transcripts after PCR amplification. Products are shown on a three percent NuSieve and one percent agarose gel stained with ethidium bromide. Lane 1 (Uncut) contains a PCR product (275 bp) derived from normal peripheral-blood mononuclear cells with primers C and D and C' and D'. Lanes 2 through 5 contain PCR products derived from unaffected or affected members of Family A and digested with the restriction enzyme DdeI. The 180 bp fragment is present only in products from affected family members.

FIG. 4A depicts the detection of the mutations using the RNase protection assay described in Example 2.

The figure shows the location within normal human β cardiac myosin heavy-chain (MHC) RNA (shaded bar) of the sequences of a proband's DNA and the riboprobe templates used in the RNase protection assay. The segments of DNA used for protection are cDNA segments 1 through 5, derived from nucleated blood cells, e.g. peripheral-blood mononuclear cell; RNA (heavy lines represent the initial PCR production, and light lines the products of a second amplification with an inner primer pair), and exons from genomic DNA (see the Examples set forth below). The eight templates used as riboprobes, numbered according to nucleotide residue, are shown in the bottom half of the panel. Segment 3421-3811 was amplified from exon 27, not mRNA as described below.

FIG. 4B shows the results of an RNase protection assay and six probands. Exon 16 was amplified from the genomic DNA of probands from Families DD, LL and L and three unrelated probands (P). The amplified DNA protects a predominant RNA fragment 310 bases long that is present in every person. Novel pairs of protected RNA fragments present in Families LL and DD (170 and 140 bases, respectively) and Family L (235 and 75 bases) result from cleavage of the riboprobe, indicating a mismatch between the sequences of the DNA of these probands and the sequence of normal myosin heavy-chain DNA.

Figure 5:
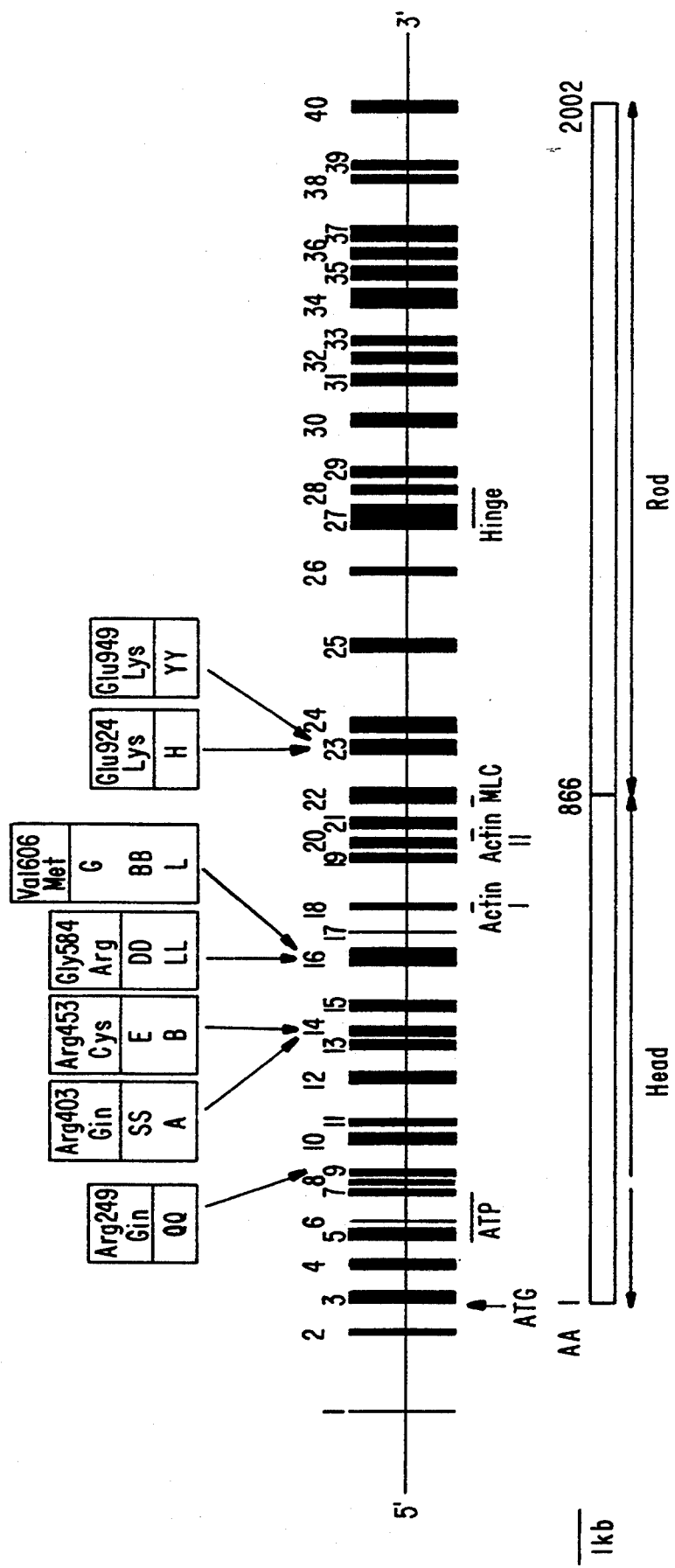

FIG. 5 depicts the location and identity of missense mutations in families with familial hypertrophic cardiomyopathy. A schematic diagram of the normal β cardiac myosin heavy-chain gene is shown in the center (5' to 3') and the location of the missense mutations is shown according to exon. The amino acid substitutions predicted by each mutation are shown in the top of each box, and the families with these mutations are designated by letters. Sequences that encode the initiation of transcription (ATG), ATPase activity (ATP), actin binding (Actin I and Actin II), myosin light-chain binding (MLC), and the hinge function (Hinge) are indicated. The head and rod regions of the encoded polypeptide are shown at the bottom of the figure.

Figure 6:
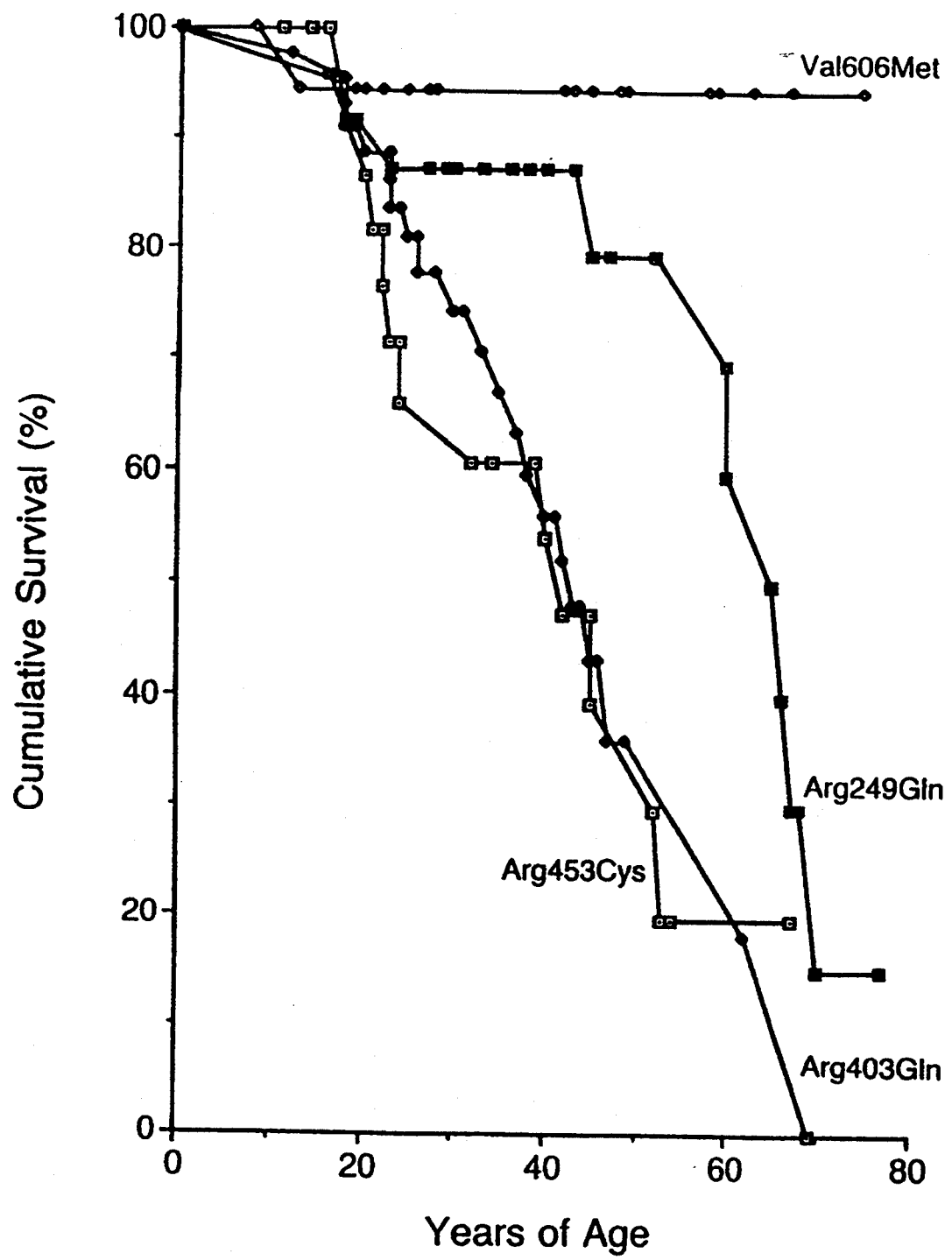

FIG. 6 depicts Kaplan-Meier product-limit curves for the survival of family members according to mutation. The curves are shown for families with each of four mutations. The curve for Arg453Cys refers to affected members in families with and without the hybrid gene.

DETAILED DESCRIPTION

The present invention pertains to a method for detecting the presence or absence of a mutation associated with hypertrophic cardiomyopathy. The method involves amplifying β cardiac myosin heavy-chain DNA to form an amplified product and detecting the presence or absence of a mutation associated with HC in the amplified product.

The term mutation for purposes of this invention is intended to include mutations associated with the respective diseases being discussed, e.g. hypertrophic cardiomyopathy. The mutation may be a gross alteration in the RNA or DNA, small alteration in the RNA and DNA, or even a point mutation in the RNA or DNA. The mutation further may be a mutation of the DNA which changes the amino acid encoded by that portion of the DNA strand, e.g. a missense mutation, or a mutation which does not change the encoded amino acid.

HC is a well characterized disorder or disease as described above. This term is intended to include both FHC or SHC. FHC is inherited throughout families and SHC occurs sporadically without a traceable hereditary path. For example, a subject having HC clinical symptoms may be diagnosed as being SHC if both of the subject's parents are actually diagnosed and determined to be healthy yet the subject has HC. Even further, if an afflicted subject's parents are not available for diagnosis and the afflicted subject has no other known family members with HC, then the subject probably would be diagnosed as having SHC.

The term amplification for purposes of this invention is intended to include any method or technique capable of amplifying the respective DNA (including culturing) or RNA being discussed. The preferred amplification technique is the polymerase chain reaction (PCR) which is an art recognized technique and most preferably the amplification is conducted using a nested PCR technique as described in the examples below.

The term β cardiac myosin heavy-chain DNA for purposes of this invention includes both genomic β cardiac myosin heavy-chain DNA and β cardiac myosin heavy-chain cDNA. The preferred β cardiac myosin heavy-chain DNA is cDNA reverse transcribed from RNA obtained from a subject being screened for the respective disorder or disease, e.g. SHC or FHC. The RNA may be obtained from cardiac or skeletal tissue or from nucleated blood cells as described below.

The detection of the presence or absence of a mutation associated with hypertrophic cardiomyopathy in the amplified product may be conducted using any method capable of detecting such mutations. Examples of conventional methods used to detect mutations in DNA sequences include direct sequencing methods (Maxim and Gilbert, *PNAS USA* 74:560-564 (1977); Sanger et al., *PNAS USA* 74:5463-5467 (1977)), homoduplex methods, heteroduplex methods, the single-stranded confirmation of polymorphisms (SSCP analysis) technique, and chemical methods. It should be understood that these methods are being provided merely to illustrate useful methods and one of ordinary skill in the art would appreciate other methods which would be useful in the present invention. The preferred detection method of the present invention is a heteroduplex method, particularly a protection assay which is similar to the RNase protection assay described by Myers et al. (*Science*, Vol 230, No. 3:1242-46 (1985)), the contents of which is expressly incorporated by reference.

A protection assay may be used to detect the presence or absence of the HC-causing mutation by combining amplified β cardiac myosin heavy-chain DNA with an RNA probe under hybridization conditions forming a hybrid double strand. The RNA probe is selected to be completely hybridizable to normal β cardiac myosin heavy-chain DNA, i.e. DNA without disease-causing mutatons. The hybridization conditions are the same or similar to those described by Myers et al., cited supra. For example, the hybridization may include the addition of the RNA probe to a solution containing the DNA, e.g. a hybridization buffer, at appropriate conditions, e.g. 90° C. for ten minutes. Subsequently, this mixture may be incubated for a longer period of time, e.g. at 45° C. for thirty minutes.

The term "completely hybridizable" for purposes of this invention is intended to include RNA probes capable of hybridizing at each nucleotide of a complementary normal DNA sequence. This characteristic of the RNA probe allows for the detection of an unhybridized portion at a mismatched or mutant nucleotide(s).

The hybrid double strand, i.e. the RNA:DNA double strand, has unhybridized portions of RNA at locations or portions corresponding to a mutation in the normal DNA strand, e.g. an HC-associated mutation. The hybrid double strand is contacted with an agent capable of digesting an unhybridized portion(s) of the RNA strand, e.g. an RNase. The presence or absence of any unhybridized portions are then detected by analyzing the resulting RNA products. The RNA products may be analyzed by electrophoresis in a denaturing gel. Two new RNA fragments will be detected if the sample DNA contained a point mutation resulting in an unhybridized portion recognizable by the RNase. The total size of these fragments should equal the size of the single RNA fragment resuting from the normal DNA. The mutation(s) can be localized relative to the ends of the RNA probe by determining the size of the new RNA products. The sequence of the mutation may be determined by looking at the localized portion of corresponding DNA.

The agent capable of digesting an unhybridized portion of the RNA strand may be any agent capable of digesting unprotected ribonucleotides in the hybrid strands. Examples of such agents include ribonucleases, particularly RNase A.

As set forth above, the method of this invention can detect the presence or absence of the mutation associated with the respective disease or even further, the position within the gene or sequence of the mutation. The sequence or position may be determined by observing fragments resulting from mutations and comparing the fragments to a known template derived from the riboprobe which is representative of normal DNA.

The present method further pertains to a method for diagnosing FHC by obtaining a sample of β cardiac myosin heavy-chain DNA derived from a subject being screened for FHC. The subject is diagnosed as having FHC by detecting the presence or absence of an FHC-causing point mutation in the β cardiac myosin heavy-chain DNA as an indication of the disease.

The term subject for purposes of this invention is intended to include subjects capable of being afflicted with HC. The preferred subjects are humans.

The present invention is based, at least in part, on the discovery that FHC is caused by point mutations in the β cardiac myosin heavy-chain gene. Prior to the present invention, there were no extensive studies involving a large number of families which established that this particular disease or disorder was caused by point mutations in the β cardiac myosin heavy-chain gene. Geisterfer-Lowrance et al. (Cell 62:999-106 (1990)) described a point mutation in exon 13 of the β cardiac myosin heavy-chain gene which was present in all individuals affected with FHC from a large family. Tanigawa et al. (Cell 62:991-998 (1990)) determined that an α/β cardiac myosin heavy-chain hybrid gene is coinherited with FHC in a different family (Family B). In view of both of these findings, it was not clear until the present invention that FHC is caused by a point mutation and not a hybrid gene.

The present invention further pertains to a non-invasive method for diagnosing hypertrophic cardiomyopathy. The method involves obtaining a blood sample from a subject being screened for hypertrophic cardiomyopathy, isolating β cardiac myosin heavy-chain RNA from the blood sample, and diagnosing the subject for hypertrophic cardiomyopathy by detecting the presence or absence of a hypertrophic cardiomyopathy-associated mutation in the RNA as an indication of the disease.

The RNA may be isolated from nucleated blood cells. Nucleated blood cells include lymphocytes, e.g. T and B cells, monocytes, and polymorphonuclear leucocytes. The RNA may be isolated using conventional techniques such as isolation from tissue culture cells, guantidinium methods and the phenol/SDS method. See Ausebel et al. (*Current Protocols in Molecular Biology* (1991), Chapter 4, Sections 4.1-4.3), the contents of which are expressly incorporated by reference.

The present invention is based, at least in part on the discovery, that normal and mutant β cardiac myosin heavy-chain RNA is present in nucleated blood cells, e.g. lymphocytes, a phenomenon called ectopic transcription. Access to RNA provides a more efficient method of screening for disease-causing mutations because intron sequences have been excised from these transcripts. This is further advantageous because cardiac myosin heavy-chain RNA is abundant in the heart and slow-twitch skeletal muscle but its expression in other tissues is extremely low (Mahdavi et al., *Nature* 297:659-64 (1982); Lomprei et al., *J. Biol Chem* 259:6437-46 (1984); and Lichter et al., *Eur J Biochem* 160:419-26 (1986)). An invasive method would be required to obtain RNA from the aforementioned muscles whereas the present invention is a non-invasive method in that the mRNA is easily obtained from a blood sample.

The present invention further pertains to a method for detecting the presence or absence of a disease-associated mutation in a DNA sequence. This method is carried out by amplifying a DNA sequence suspected of containing a disease-associated mutation forming an amplified product, and combining the amplified product with an RNA probe completely hybridizable to a normal DNA sequence associated with the disease forming a hybrid double strand having an RNA and DNA strand. The hybrid double strand has unhybridized portions of the RNA strand at any portions corresponding to a disease associated mutation in the DNA strand. The presence or absence of an unhybridized portion of the RNA strand is detected as an indication of the presence or absence of a disease associated mutation in the corresponding portion of the DNA strand. The presence or absence of an unhybridized portion of the RNA strand may be detected by contacting the hybrid double strand with an agent capable of digesting an unhybridized portion of the RNA strand, denaturing the hybrid double strand, separating the RNA fragments by size, and detecting the presence or absence of fragments of RNA resulting from portions of an RNA strand being digested by the agent. The method further may include the sequencing of a portion of DNA corresponding to an unhybridized portion of the RNA strand to identify the sequence of a disease-associated mutation. More than one mutation also may be detected using the method of the present invention.

Many diseases have already been established as being associated with a mutation in the DNA sequence, e.g. a particular gene. A disease associated mutation for purposes of this invention includes a mutation linked to or believed to be at least part of the causative factor for the disease. Some diseases associated with mutations have been described in Antonarakis, cited supra, the contents of which is expressly incorporated by reference. Antonarakis describes an expansive list of disorders or diseases, the gene associated with such diseases, the location on a particular chromosome of the gene, and the types of mutations. Some of the diseases associated with mutations and particular genes are as follows: (each disease is followed by the respective gene) Gaucher's disease (glycocerebrosidase), Factor XIII deficiency (Factor XIII), diabetes mellitus due to abnormal insulins (insulin), sickle cell anemia, β-thalassemia (β-globin), McArdle's disease (muscle glycogen phosphorylase), phenylketonuria (phenylalanine hydroxylase), Tay-Sachs disease ($α_1$-hexosaminidase), α-thalassemia (α-globin), Duchenne's muscular dystrophy (gene for Duchenne's muscular dystrophy), hemophilia B (Factor IX), and hemophilia A (Factor VIII). It should be understood that the method of this invention may also be used for detecting a mutation associated with HC as described above.

The present invention also pertains to a method for determining the estimated life expectancy of a person having FHC. The method involves obtaining β cardiac myosin DNA derived from a subject having FHC and detecting a FHC-causing point mutation. The point mutation subsequently is classified as a particular type and the life expectancy of the subject is estimated using a Kaplan-Meier curve for the classified type of mutation. This aspect of the invention is described in more detail below.

The present invention also pertains to kits useful for diagnosing HC. The kit contains a first container such as a vial holding an RNA probe and a second container holding primers. The RNA probe is completely hybridizable to β cardiac myosin heavy-chain DNA and the primers are useful for amplifying β cardiac myosin heavy-chain DNA. The kit further may contain an RNA digesting agent or instructions for using the components of the kit to detect the presence or absence of HC-associated point mutation in amplified S cardiac myosin heavy-chain DNA. The RNA probe and primers also are intended to be part of this invention.

The following examples are being provided to further illustrate the above-described invention and should in no way be construed as being further limiting to the present invention. The entire contents of all of the references mentioned in the below examples are expressly incorporated by reference. The entire contents of Rozensweig et al. (*New England Journal of Medicine* 325:1753–60 (Dec. 19, 1991)) and Watkins et al. (*New England Journal of Medicine* 326:1108–1114 (Apr. 23, 1992)) also are expressly incorporated by reference.

EXAMPLE 1 - The Detection of a Missense Mutation in the β Cardiac Myosin Heavy-Chain Gene in Members from Family A and Family QQ General Methodology Cell Lines and DNA and RNA Extraction Blood was drawn from members of Family A and normal control subjects. The blood samples were used to prepare DNA from red-cell pellets (Gross-Bellard et al., *Eur. J. Biochem.* 36:32-8 (1973)) and to establish lymphoblastoid cell lines (Holcombe et al., *Genomics* 1:287-91 (1987)). RNA was prepared from fresh peripheral-blood mononuclear cells or Epstein-Bart virus-transformed cell lines by acid guanidinium thiocyanate-phenol-chloroform extraction (Chomczynski et al., *Anal. Biochem,* 162:156–9 (1987)).

PCR and Restriction Enzyme and Sequence Analysis

Nested PCR (Sarkar et al., *Science* 244:331–4 (1989)) was used to amplify β cardiac myosin heavy-chain RNA from fresh peripheral-blood mononuclear cells and cell lines transformed by Epstein-Barr virus (see FIG. 1A). One to 2 μg of total RNA was reverse-transcribed with Moloney murine leukemia virus reverse transcriptase (Bethesda Research Laboratories) with 0.5 μg of the antisense primer from the outer primer pair. The first round of amplification was then performed by the addition of 0.5 μg of the outer sense primer (FIG. 1A, A or C) and 0.2 mmol of each deoxynucleoside triphosphate (Pharmacia) in a volume of 100 μl (final dilution, 1:1000) containing 10 mmol of TRIS-hydrochloric acid (pH 8.3), 50 mmol of potassium chloride, 1.5 mmol of magnesium chloride, and 0.01 percent (wt/vol) gelatin. Forty cycles were carried out in a thermocycler (Perkin-Elmer Cetus) under the following conditions: 0.5 minute of denaturation at 94° C., one minute of primer annealing at 55° C., and two minutes of primer extension at 72° C. PCR products were then diluted 1:100 and 10 μl was used as the template for the reaction in a volume of 100 μl of PCR buffer for Amplitaq (sold by Perkin-Elmer) (final dilution, 1:1000), in which the inner primer pair (FIG. 1A, A' and B' or C' and D') was used for an additional forty cycles. After the second reaction, 10 μl of the PCR product was electrophoresed on a two percent agarose gel to confirm amplification. To avoid contamination of the PCR products, positive displacement or filtered pipette systems were used and a number of negative controls were run with each amplification. Restriction analysis of these products was performed according to previously described techniques (Ausebel et al, *Current Prtocols in Molecular Biology*, 1989; Sanbrook et al, *Molecular Cloning: A Laboratory Manual*, Cold Spring Harbors, 1989). The PCR products were sequenced by performing an additional round of asymmetric amplification (Ausebel et al, cited supra (1989)) followed by direct sequence analysis, as previously described for single-stranded products (Sanger et al. PNAS USA 74:5463-7 (1977)). Genomic DNA was amplified for thirty five cycles with primers B9.1F and B9.1R, including denaturation for 0.5 minutes at 94° C., primer annealing for one minute at 55° C. and primer extension for one minute at 72° C. The sequences of the PCR primers were as follows: A, 5'CAAGGATCGCTACGGCTCCTGGAT3'(SEQ. ID NO:1) B, 5'GCGGATCCAGGTAGG-CAGACTTGTCAGCCT3'(SEQ. ID NO:2), A', 5'ATGCCAACCCTGCTCTGGAGGCCT3'(SEQ. ID NO:3); B', 5'CTTCATGTTTCCAAAGTGCAT-GAT3'(SEQ. ID NO:4); C, 5'CTGGGCTTCACTT-CAGAGGAGAAAA3'(SEQ ID NO:5); D, 5'GCGGTACCCCAGCAGCCCGGCCTT-GAAGAA3'(SEQ ID NO:6); C', 5'GGGAATTCGC-GGAGCCAGACGGCACTGAAG3'(SEQ. ID NO:7); D', 5'CCCTCCTTCTTGTACTCCTCCTGCTC3'(SEQ ID NO:8); B9.1F, 5'CAACTCATCACCACTCTCTT-CCATC3'(SEQ. ID NO:9); and B9.1R, 5'GCTGAGC-CTAGCAGATTCATGGCAC3'(SEQ. ID NO:10).

RNase Protection

Figure 2A:
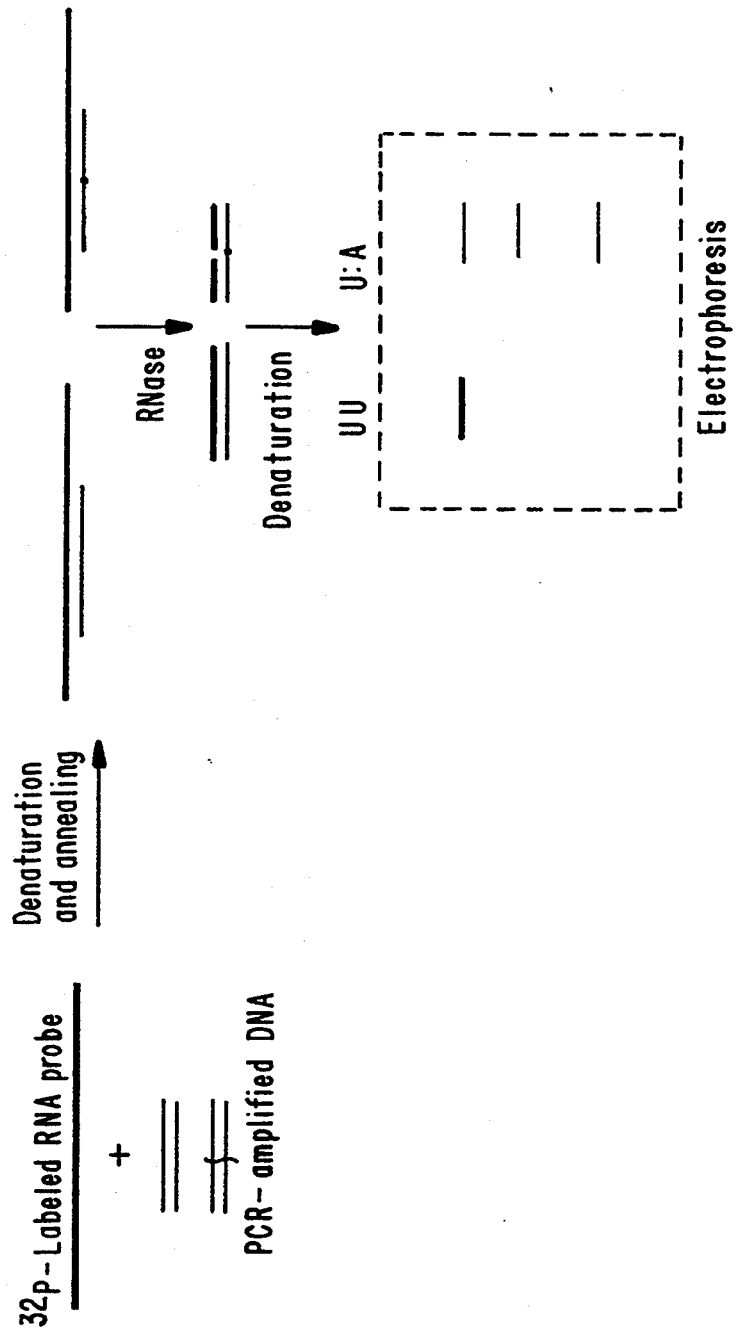
FIG. 2A is a schematic showing the identification of mutations in the β cardiac myosin heavy-chain gene using an RNA protection assay. A $^{32}$P-labeled RNA probe (shown in FIG. 1A) was transcribed in vitro from a fragment of wild-type β cardiac myosin heavy-chain cDNA. Amplified products generated by nested PCR were hybridized to the RNA probe, and the resulting RNA-DNA hybrid was digested with RNase A. Overhanging ends of the probe and mismatched bases (hatched areas) were digested by RNase A. Digestion products were analyzed by denaturing acrylamide-gel electrophoresis. The results of electrophoresis is shown in the box. Samples from homozygous, unaffected persons (U/U) contained amplified fragments homologous to the β cardiac myosin heavy-chain RNA probe (single bold band). Samples from heterozygous, affected persons (U/A) contained these fragments (upper band) and new fragments (two lower bands) resulting from internal cleavage at the site of the mismatch between the wild-type β cardiac myosin heavy-chain probe and products amplified from the mutant gene.

RNase protection was performed as described by Myers et al. (*Science* 230:1242–6 (1985)) with the use of volumes scaled down threefold (see FIG. 2A). First, PCR-amplified product (4 ul) was hybridized to a $^{32}$P-labeled RNA probe (200,000 counts per minute) and the resulting RNA-DNA hybrid was then digested with RNase A (Sigma) and analyzed by denaturing acrylamide-gel electrophoresis. RNase reactions were stopped by the simultaneous addition of proteinase K and sodium dodecyl sulfate and 15 μl of the final product was added to 20 μl of loading buffer for electrophoresis without phenol-chloroform extraction or ethanol precipitation.

Clinical Evaluation

Family members were evaluated by physical examination, 12-lead electrocardiography, Doppler ultrasonography, and two-dimensional echocardiography, with left and right ventricular views (Maron et al., *Am J Cardiol* 48:418–28 (1981); Shapiro et al., *J Am Coll Cardiol* 2:437–44 (1983); McKenna et al., 11:351–8 (1988)). Electrocariograms were interpreted according to standard criteria (Surawicz et al., *Am J Cardiol* 41:130–45 (1978)). Echocardiographic measurements of wall thickness and cavity dimensions and the presence or absence of systolic anterior motion of the mitral valve were determined according to established protocols (Maron et al., cited supra; Shapiro et al., cited supra; McKenna et al., cited supra; Wigle et al. *Prog Cardiovasc Dis* 28:1–83 (1985)). The diagnosis of familial hypertrophic cardiomyopathy was based on the demonstration of unexplained ventricular hypertrophy. Clinical diagnoses were made by two experienced clinicians who had no knowledge of the genotypic results. None of the family members evaluated had a history of systemic hypertension or a blood pressure higher than 140/90 mm Hg at rest.

The above-described general methodology was used in the example set forth below on samples obtained from members of Family A and control subjects.

Determination of Whether the β Cardiac Myosin Heavy-Chain Gene is Ectopically Expressed in Blood Mononuclear Cells It was decided to determine whether there was ectopic expression of the β cardiac myosin heavy-chain gene in blood mononuclear cells. A strategy of nested PCR amplification was used to detect extremely low levels of β cardiac myosin heavy chain mRNA as shown in FIG. 1A. Reverse transcriptase was used to obtain the cDNA from RNA extracted from peripheral blood mononuclear cells or cells transformed by Epstein-Barr virus. The cDNA was used as a template in the initial round of PCR. After the first round of amplification with primers C and D (or A and B), no specific product was visible on ethidium bromide staining. A second round of PCR was then performed with internal primers C' and D' (or A' and B') after a 1000-fold dilution of the initial products. Sequential amplification yielded a product of 275 base pairs (see FIG. 1B, line 1), which is the size predicted for the β cardiac myosin heavy-chain sequence. Partial nucleotide-sequence analysis was performed on several PCR-generated fragments to demonstrate that the products obtained were derived specifically from the β cardiac myosin heavy-chain gene. The sequence was identical to that previously published by Jaenicke et al. (*Genomics* 8:194–206 (1990)).

Determination Whether Mutated As Well As Normal Transcripts of the β Cardiac Myosin Heavy-chain Gene Are Detectable In Peripheral Blood Mononuclear Cells It was decided to determine whether mutated as well as normal transcripts of the β cardiac myosin heavy-chain gene could be detected in peripheral-blood mononuclear cells. Samples obtained from a family with familial hypertrophic cardiomyopathy (Family A) were analyzed. Affected members of this family previously were shown to have a missense mutation in exon 13 of the β cardiac myosin heavy-chain gene that creates a novel DdeI restriction-enzyme site (Geisterfer-Lowrance et al., *Cell* 62:999–1006 (1990)). RNA was prepared from Epstein-Barr virus-transformed cells from both affected and unaffected member of Family A and sequentially amplified with primers C and D followed by C° and D' (FIG. 1A). The amplified product was then digested with the restriction enzyme DdeI and fractionated according to size on an argarose gel. The digested samples from unaffected persons produced two fragments. The larger of these fragments was readily visible on ethidium bromide staining and consisted of approximately 215 bp (see FIG. 1B, lanes 2 and 4). The digested samples from affected persons yielded a third visible fragment consisting of approximately 180 bp (see FIG. 1B, lanes 3 and 5), in addition to those present in unaffected persons. The third visible fragment is of a size which is predicted by the additional DdeI site conferred by this mutation for FHC. Ectopic transcription of both the normal and the mutant allele was therefore evident in affected persons, as expected in an autosomal dominant disorder. Amplification of mutant and normal sequences should occur with equal efficiencies. The intensity of the ethidium bromide staining of the fragments, therefore, accurately reflects the relative abundance of these two transcripts and demonstrates that the mutant and normal alleles were transcribed equally in cell lines transformed by Epstein-Barr virus.

The detection of transcripts from both normal and mutant β cardiac myosin heavy-chain genes in peripheral-blood cells provides a mechanism for the rapid identification of mutations that cause FHC. The detection of both normal and mutant genes is particularly important for FHC because, unlike disorders such as sickle cell anemia, different β cardiac myosin heavy-chain mutations can cause the disease in unrelated families.

Figure 2B:
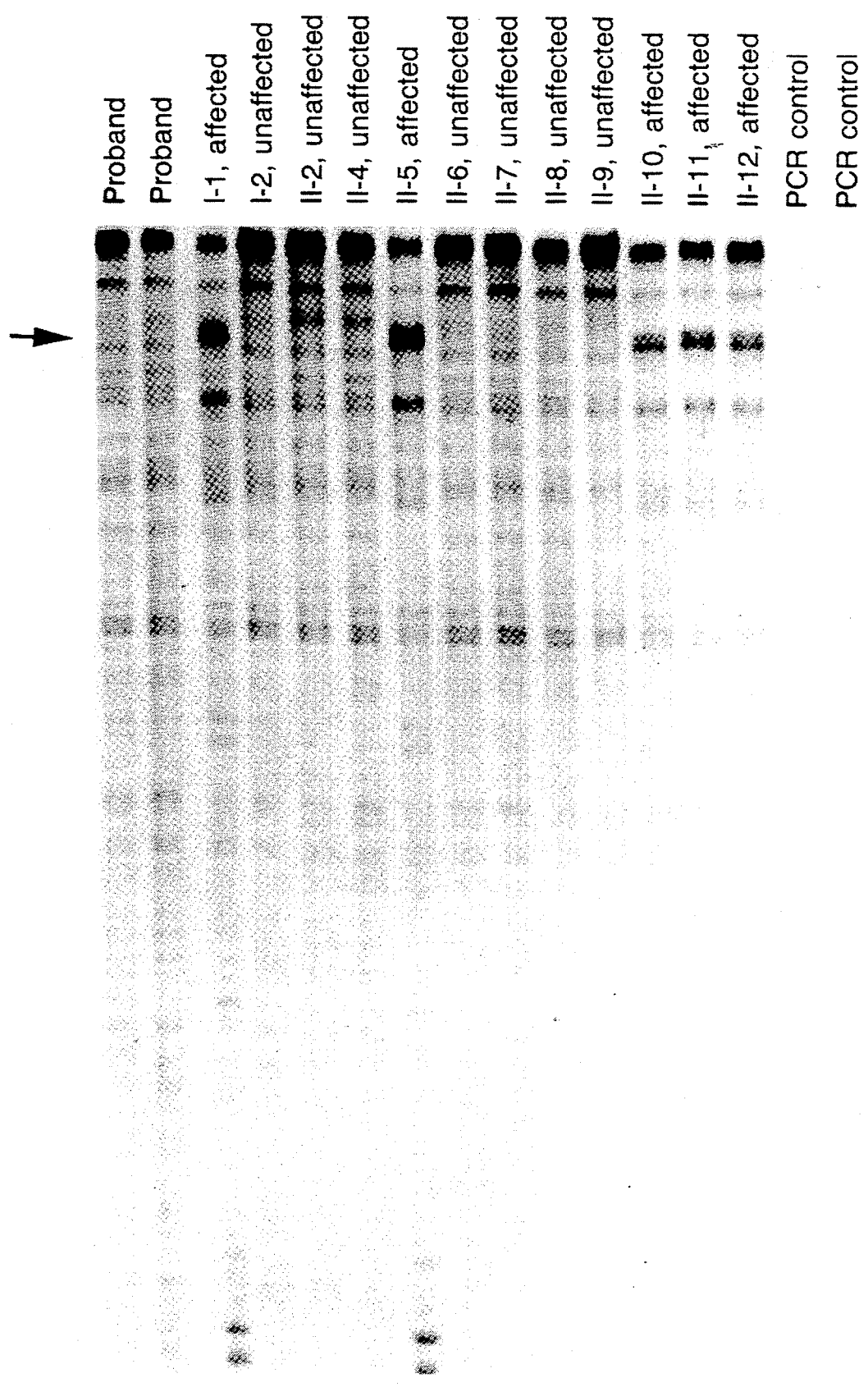
FIG. 2B is a photograph showing the results of the RNA protection assay in two affected probands and in members of Family QQ. Products of nested PCR obtained with primers A and B and A' and B' (shown in FIG. 1A) were analyzed in an RNase protection assay with the riboprobe shown in FIG. 1A. Samples from two unrelated, affected probands are shown in lanes 1 and 2. Lanes 3 through 14 contain samples from members of Family QQ, identified according to the pedigree shown in FIG. 3 and disease status. The RNase protection assay identified a novel fragment (arrow) in family member I-1 that is present only in affected members of Family QQ. The PCR controls produced no fragments visible on ethidium bromide staining of agarose gel and did not protect the β cardiac myosin heavy-chain RNA probe.

Assessing the Usefulness of Detection Method for New β Cardiac Myosin Heavy-Chain Mutations in Family QQ RNA was isolated from Epstein-Barr virus-transformed cell lines derived from affected persons in different, unrelated families. RNA samples were used as the template in PCRs with nested primers (FIG. 1A, A and B followed by A' and B'), and the amplified test strands of DNA were hybridized to a β cardiac myosin heavy-chain RNA probe (FIG. 1A) for RNase protection assays (FIG. 2B). The RNase protection assay yielded fragments which formed a complex pattern of bands, however, novel fragments were easily identified because of the homogeneity of patterns in unrelated probands (see FIG. 2B, lanes 1 through 3). A unique band was present in the sample analyzed in lane 3 of FIG. 2B. A second RNA sample from this person was analyzed to exclude the possibility that this band arose because erroneous sequences were introduced during sequential PCRs. This analysis confirmed the presence of a new band implying a sequence difference between the affected person's DNA and DNA from an unaffected person. All other peptide-encoding regions of the β cardiac myosin heavy-chain gene was screened and no other abnormalities were detected in this person.

Figure 3A:
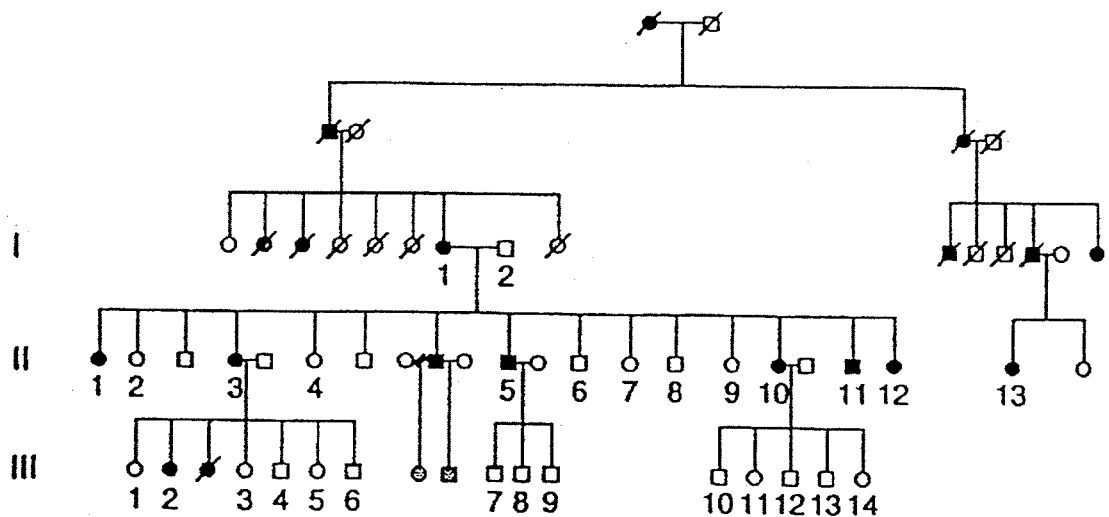
FIG. 3A is a schematic showing family pedigree of Family QQ. Male family members are denoted by squares, female members by circles, deceased members by a slash, affected members by solid symbols, unaffected members by open symbols, and members whose disease status undetermined by stippled symbols. The disease status was based on clinical analysis. Numbered family members were available for clinical and genetic evaluation.

The persons family (Family QQ) was studied to determine whether the sequence difference is coinherited with disease status (part of the pedigree is shown in FIG. 3A). Ten affected family members had died of hypertrophic cardiomyopathy before the study. Four of the deaths were sudden. Clinical evaluations of adult family members (generations I and II) identified eight affected persons (age, 28 to 68 years). Four of the family members were asymptomatic. All had abnormal electrocardiograms. Seven had typical left ventricular hypertrophy on two-dimensional echocardiography, with a maximal left-ventricular-wall thickness of 1.5 to 2.5 cm (mean, 2.2). Family member II-11 had apical left ventricular hypertrophy on two-dimensional echocardiography, but a maximal left-ventricular-wall thickness of 1.0 cm and mild mitral regurgitation. The left atrial dimension was increased in all eight affected members (4.0 to 5.1 cm; mean, 4.5). None of the family members had complete systolic anterior motion of the mitral valve or evidence of a left ventricular gradient on Doppler ultrasonography. Samples from all adults who were clinically affected on the basis of two-dimensional echocardiography were analyzed. All of the affected family members had a band that was absent from samples derived from unaffected adult family members which represents a mutation in the β cardiac myosin heavy-chain gene. FIG. 2B (lines 3 through 14) shows the results of RNase protection assays for several adults in this family. The family members are designated using the symbols from the family pedigree depicted in FIG. 3A.

The sequence difference detected by the RNase protection assay in family member I-1 (the arrow in FIG. 2B) also was present in all other affected members of Family QQ. There was complete concordance between clinical and molecular genetic diagnoses in all members of generations I and II. The probability of obtaining this result by chance (i.e., if the mutation and disease were not linked) is 1 in 10,000 (lod score, 4.0 at $\theta=0$).

The difference in the nucleotide base pair that accounts for the novel band in the RNase protection assays was identified by nucleic acid sequence analysis of this region of the β cardiac myosin heavy-chain gene derived from family member I-1. A guanine residue normally present at position 832 (exon 9) was converted to an adenine residue. This missense mutation creates a nonconservative amino acid substitution of glutamine for arginine (position 249), which results in a change in charge from +1 to 0. This amino acid substitution was not previously identified among 100 normal chromosomes or 50 chromosomes from unrelated patients with FHC. Furthermore, this arginine residue has been stringently conserved throughout evolution and is invariant in all muscle myosins characterized to date (Jaenicke et al., cited supra; Liew et al., *Nucleic Acids Res.* 18:3647-51 (1990); Dibb et al., *J Mol Biol* 205:603-13 (1989); Jung et al. *Gene* 82:269-80 (1989); Karn et al., *Proc Natl Acad Sci* USA 80:4253-7 (1983); McNally et al., *J Mol Biol* 210:665-71 (1989); Molina et al., *J Biol Chem* 262:6478-88 (1987); Rozek et al., *Proc Natl Acad Sci* USA 83:2128-32 (1986); Shohet et al., *Proc Natl Acad Sci* USA 86:7726-30 (1989); Stedman et al., *J. Biol Chem* 265:3568-76 (1990); Strehler et al., *J Mol Biol* 190:291-317 (1986); Tong et al. *J Biol Chem* 265:2893-901 (1990); Yanagisawa et al., *J Mol Biol* 198:143-57 (1987)).

Figure 3B:
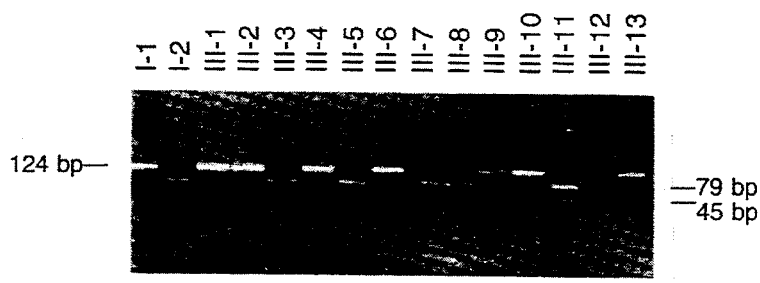
FIG. 3B shows the results of the genetic analysis of generation III. Genomic DNA was extracted from two independent blood samples obtained from members of Family QQ and amplified by PCR with primers B9.1F and B9.1R. Products were digested with the restriction enzyme EcoR1 and fractionated according to size on a three percent NuSieve and one percent agarose gel stained with ethidium bromide. Samples from persons with the normal sequence contained two fragments consisting of 79 and 45 bp. Samples from persons with the mutant sequence contained these fragments and the full-length 124 bp fragment because the QQ mutation abolishes the internal EcoR1 site. Analysis of family member III-14 was performed independently.

The missense mutation abolishes an EcoRI restriction-enzyme site normally present in exon 9 (Jaenicke et al, cited supra and Liew et al., cited supra) which provides an independent method of assessing genetic diagnoses. Exon 9 sequences of the β cardiac myosin heavy-chain gene were amplified with the use of whole-blood DNA. The PCR products were digested with EcoRI and fractionated according to size on agarose gels. The normal sequence produced two fragments that were 79 and 45 bp long. The mutated sequence lacked this EcoRI site and therefore half of the PCR product derived from affected persons was uncut (FIG. 3B, lane 1, showing results for affected member I-1, as compared with lane 2, showing results for unaffected member I-2). In each sample, two small fragments derived from the normal allele were present. An additional larger fragment was visible in the sample from family member I-1, confirming the loss of an EcoRI restriction-enzyme site in the mutant sequence. All adult family members were assessed by this method, and as with RNase protection assays, there was complete agreement between clinical and genetic disease assignment.

Fourteen children of affected parents in this family were evaluated to determine whether accurate diagnosis based on genetic technique is possible without clinical evidence of FHC. None of these children, who ranged in age from 1 to 20 years, were previously known to be affected and none had symptoms suggestive of FHC. Their two-dimensional echocardiographic and electrocardiographic findings are shown in Table I below.

TABLE 1

Results of Clinical and Genetic Analysis of Generation III of Family QQ.

| Family Member | Age (Yr) | 2-Dimensional Echocardiogram | Electrocardiogram | Geno-Type |
|---|---|---|---|---|
| III-1 | 20 | Normal | Abnormal Q wave, inferior T-wave inversion | + |
| III-2 | 19 | Septal and free-wall hypertrophy | Left ventricular hypertrophy inferior T-wave inversion | + |
| III-3 | 16 | Normal | Normal | − |
| III-4 | 14 | Normal | Left ventricular hypertrophy inferior T-wave inversion | + |
| III-5 | 12 | Normal | Normal | − |
| III-6 | 7 | Normal | Inferior T-wave inversion | + |
| III-7 | 14 | Normal | Normal | − |
| III-8 | 11 | Normal | Normal | − |
| III-9 | 2 | Normal | Normal | + |
| III-10 | 8 | Normal | QRS complex prolonged for age | + |
| III-11 | 6 | Normal | Normal | − |
| III-12 | 4 | Normal | Normal | + |
| III-13 | 3 | Normal | Normal | − |
| III-14 | 1 | Normal | Normal | − |

Only one child (III-2) had findings diagnostic of FHC. Two children (III-1 and III-4) had subtle features of focal hypertrophy noted by one investigator but a definite clinical diagnosis for FHC could not be made. Five children had electrocardiographic abnormalities, including left ventricular hypertrophy (III-2 and III-4), abnormal Q wave (III-1), T-wave abnormalities (III-1, III-2, III-4, and III-6) and a QRS complex that was longer than expected for age (III-10) (Perry et al., *J. Pediatrics* 97:677-87 (1980)). A genetic diagnosis, based on a 5-ml blood sample, was made in all 14 children without knowledge of the clinical findings. DNA digestion with the restriction enzyme EcoRI (FIG. 3B, lanes 3-15) and RNase protection assays were performed on PCR products amplified from exon 9. Each analysis identified seven children with a missense mutation of the β cardiac myosin heavy-chain gene at amino acid residue 249, and the results were completely concordant. These seven children included all children with any abnormalities present on two-dimensional echocardiograms or electrocardiograms. A genetic diagnosis of FHC was also made in two children (III-9 and III-12; ages 2 and 4 years) who had completely normal clinical studies.

Clinical Evaluation

Blood samples were obtained from the respective family members. Clinical, electrocardiographic, and echocardiographic assessments were performed as previously described (Jarcho et al., cited supra). The diagnosis of hypertrophic cardiomyopathy was based on he demonstration of unexplained hypertrophy of either ventricle or both ventricles. Clinical records, family histories, or both were obtained to determine the number of disease-related deaths, the number of sudden deaths (disease-related deaths due to unexpected cardiac arrest or abrupt circulatory collapse), and the age at death or the current age of all affected members of each family. Kaplan-Meier product-limit survival curves were produced as described elsewhere (Kaplan et al., *J. Am. Stat. Assoc.* 53:457–81 (1958); Lee, "Statistical Methods for Survival Data Analysis", Belmont, Calif., Lifetime Learning Publications, (1980)). These curves were compared according to the log-rank method of Peto and Peto (Cox et al., "Analysis of Survival Data", London, Chapman and Hall, (1984)). All P values were calculated with the assumption of a two-tailed distribution.

Strategy for the Detection of Mutations

The polymerase chain reaction (PCR) was used to amplify the sequences of β cardiac myosin heavy-chain genes derived from RNA isolated from nucleated blood cells obtained from affected family members that were transformed by the Epstein-Barr virus (FIG. 4A). Both normal and mutationally altered β cardiac myosin heavy-chain RNA were detected in these cell lines as described above. Amplified sequences were hybridized to RNA probes derived from an unaffected member, and an RNase A protection assay was performed as described above. Both sense and antisense riboprobes were used to increase the probability of identifying all mutations. The entire β cardiac myosin heavy-chain coding sequence of each proband was examined to determine whether any of these sequences contained more than one mutation. Amplified DNA samples yielding abnormal RNase cleavage patterns were reanalyzed with new DNA isolates to exclude artifacts arising from the PCR and were then subjected to nucleotide-sequence analysis. Throughout this example, mutations are denoted by the three-letter code for the normal amino acid, followed by the residue number and the code for the predicted amino acid sequence resulting from each mutation.

Templates for the Riboprobes

Twenty-five base oligonucleotide primers (containing nucleotide sequences as numbered by Jaenicke et al., cited supra and a selected restriction-enzyme site) were used to reverse-transcribe and amplify seven segments of normal human β cardiac myosin heavy-chain RNA (FIG. 4A). One segment (3421 through 3811) could not be amplified from RNA with PCR and was produced by amplifying exon 27 from human DNA. Each amplified product was cloned into a Blue-script SK vector (Stratagene) according to standard procedures (Ausubel et al., Current Protocols in Molecular Biology, N.Y., Green Publishing, 1989 (1991 update)). The eight different β cardiac myosin heavy-chain clones were linearized by restriction-enzyme digestion and transcribed with the use of T3 or T7 RNA polymerase.

DNA for Screening

Segments of β cardiac myosin heavy-chain cDNA were obtained by nested PCR amplification of cDNA reverse-transcribed from peripheral-leukocyte RNA as described above, or individual exons were amplified from genomic DNA. cDNA segments, numbered 1 through 6 (FIG. 4A) were amplified with the former approach. The diluted product from an initial PCR amplification with outer primers was used as the template for a second round of PCR amplification with an inner-primer pair. This technique could not be used throughout the example because of difficulties in amplifying some RNA sequences encoding the rod region. These areas were screened by amplifying the sequences of individual exons. Section 1203 through 2398 (corresponding to exons 13 through 20) was screened with DNA templates produced according to both techniques, with identical findings.

The following nucleotide numbers are those of the primers used in the nested PCR amplification of cDNA (all were 25-mers, each numbered by its 5' residue according to the cDNA sequence (Jaenicke et al., cited supra); see FIG. 4A; 1, outer 20 to 475, inner 50 to 450; 2, outer 401 to 1235, inner 425 to 800 and 750 to 1175; 3, outer 750 to 1700, inner 1101 to 1600; 4, outer 1501 to 2450, inner 1526 to 2025 and 1925 to 2424; 5, outer 2300 to 3301, inner 2325 to 2825 and 2726 to 3276; and 6, outer 4401 to 5105, inner 4449 to 5080. The following are the primers for the exons (all 25-mers, each numbered by its 5' residue according to the gene sequence (Jaenicke et al., citeed supra)): 27, 19178 to 19597; 28, 19740 to 20048; 29, 20101 to 20279; 30, 20973 to 21257; 31, 21689 to 21954; 32, 22033 to 22313; 35, 23567 to 23848; 36, 23902 to 24088; 37, 24123 to 24457; 38, 25293 to 25470; 39, 25508 to 25698; and 40, 26539 to 26724.

Linkage Analyses

Sequence variants identified in a proband were used to assess genetic linkage between the disease status of family members and the β cardiac myosin heavy-chain gene. Lod (logarithm of the odds) scores were calculated with the LINKMAP program (Lathrop et al., *PNAS USA* 81:3443-6 (1984), for a recombination fraction ($\theta$) of 0.0, with a penetrance of 0.95 and an allele frequency of the sequence variant of 0.05. Lod scores of families with the same mutation were combined. A lod score greater than 1.3 indicates that the odds in support of linkage are higher than 20 to 1.

Study of Twenty-five Kindreds with Familial Hypertrophic Cardiomyopathy

EXAMPLE 2 - Determination of the Proportion of Families with Hypertrophic Cardiomyopathy Caused By Myosin Heavy-Chain Mutations Twenty-five families were studied whose members have hypertrophic cardiomyopathy. Preliminary research had indicated that major structural abnormalities of the α or β cardiac myosin heavy-chain genes are not a common cause of FHC. RNase protection assays therefore were used to screen directly for point mutations or other small alterations in the β cardiac myosin heavy-chain gene which encodes the predominant isoform of myosin expressed in the ventricles of adults (Mahdavi et al., *Nature* 297:659-64 (1982); Lomprei et al., *J Biol. Chem.* 259:6437-46 (1987)). The following general methodology was used in the example below.

The affected members of these twenty-five families have features typical of hypertrophic cardiomyopathy as assessed by physical examination, two-dimensional Doppler echocardiography and electrocardiography. The disease was inherited as an autosomal dominant trait in all cases, as documented by the history or clinical evaluation (or both) of relatives. The families were of European descent and were unrelated. In three of the families (A, B, and QQ), the disease locus was known or believed to be linked to chromosome 14 band q1 from Example 1 above and Geisterfer-Lowrance et al. (Cell 61:999–1006 (1990)). The chromosomal linkage of the disease locus in all of the other families was unknown. A mutation had been previously identified in Families A and B from a limited analysis of the β cardiac myosin heavy-chain gene (Geisterfer-Lowrance et al., cited supra and Example 1 above. One proband was selected from each family for genetic analysis. A proband is derived from an affected member of a family who is selected as the representative subject for study. The entire coding sequence of the β cardiac myosin heavy-chain gene was screened to identify mutations in these probands using RNase protection assays. These assays identified nine different variants from the normal sequence of the β cardiac myosin heavy-chain gene. These nine variants were found in fourteen of the probands and two of these variants are shown in FIG. 4B.

The nine variants were characterized by nucleotide-sequence analysis. All the variants corresponded to single-nucleotide substitutions. Eight of the variants were transitions (G to A, or C to T) and one was a transversion (G to C). Six of the eight transitions occurred at a CG dinucleotide which is a common site of mutations in human disease loci (Youssoufian et al., Am. J. Hum. Genet. 42:718–25 (1988); Green et al., Nucleic Acids Res 18:3227–31 (1990); Rideout et al., Science 249:1288–90 (1990)). Seven DNA variants changed the coding sense of the β cardiac myosin heavy-chain gene (FIG. 5) and two did not alter the encoded amino acid sequence. These two variants were silent polymorphisms, both of which were found in unaffected family members. All seven variants that changed the coding sense affected residues in the amino-terminal half of the β cardiac myosin heavy-chain polypeptide (FIG. 5). Four variant sequences were found in two or more probands. These included the mutation of arginine to glutamine at residue 403 (Arg403Gln), which was initially detected in affected members of Family A (Geisterfer-Lowrance et al., cited supra) and is also found in the proband from Family SS.

There are three findings that support the position that the seven sequence variants were mutations causing FHC. First, there was complete concordance between genotype and disease status in all adult relatives of each proband in whom a mutation was identified. Linkage analyses provided statistically significant information about six of the seven mutations since many affected families were large (see Table II below).

TABLE 2

β Cardiac Myosin Heavy-Chain Gene Mutations and Associated Laboratory and Clinical Features in Families with Familial Hypertrophic Cardiomyopathy.

| Feature | Arg249 Gln | Arg403 Gln | Arg453 Cys | Arg453 Cys + HYBRID | Gly584 Arg | Val606 Met | Glu924 Lys | Glu949 Lys |
|---|---|---|---|---|---|---|---|---|
| Nucleotide change* | G832A | G1294A | C1443T | C1443T | G1836C | G1902A | G2856A | G2931A |
| Change in charge | −1 | −1 | −1 | −1 | +1 | 0 | +2 | +2 |
| Families affected | QQ | A, SS | E | B | LL, DD | L, BB, G | H | YY |
| Lod score | 4.0 | 15.9 | 3.9 | 4.4 | 1.4 | 3.5 | 1.1 | 2.2 |
| No. of members affected | 24 | 44 | 13 | 13 | 5 | 18 | 2 | 2 |
| Mortality | | | | | | | | |
| No. of disease-related deaths | 10 | 21 | 9 | 4 | 2 | 1 | 0 | 0 |
| No. of sudden deaths | 4 | 9 | 6 | 2 | 2 | 1 | 0 | 0 |
| Average age at death (yr) | 49 ± 22 | 33 ± 15 | 30 ± 12 | 35 ± 17 | 19 ± 6 | 13 | — | — |

*These mutations are designated by the normal residue and its position (numbered as described by Jaenicke et al.) followed by the mutant residue.
Values are changes in the net charge of the polypeptide, based on charges of the amino acid at pH7.
The average age at death was calculated for all deaths related to familial hypertrophic cariomyopathy. Plus-minus values are means ±SD.

Differences in lod scores reflected only differences in family size because these analyses were fully informative for all members. Second, each sequence variant predicted that the encoded amino acid residue would be altered and each altered amino acid was one that has been entirely conserved during the evolution of a vertebrate striated muscle implying functional importance. Third, these variants were not found in analyses of more than 180 normal chromosomes.

Previous studies of Family B demonstrated that affected members had an α/β cardiac myosin heavy-chain hybrid gene in addition to nonrearranged α and β myosin heavy-chain genes (Tanigawa et al., Cell 62:991–8 (1990)). The proband from this family was included in the above-described analyses and the Arg453Cys mutation was identified in a nonrearranged β cardiac myosin heavy-chain gene. This mutation was also identified in affected members of an unrelated family, Family E, all of whom lacked the hybrid gene. The natural history of the disease in affected members of these two families appeared to be similar. It was determined that the missense mutation and not the hybrid gene was responsible for the FHC in both families. Because the Arg453Cys mutation occurred in affected members of two unrelated families who had a similar phenotype, Comparaison of the Spectrum of Clinical Features In Affected Members of Families With Particular Mutations of the β Cardiac Myosin Heavy-Chain Gene The spectrum of clinical features of FHC was compared in affected members of families in which a mutation of the β cardiac myosin heavy-chain gene was identified. The incidence of angina, dyspnea, and syncope among members of a family with a given mutation was indistinguishable from the incidence among members of families with different mutations. The severity of ventricular hypertrophy as assessed by two-dimensional echocardiography also was indistinguishable among families with different mutations. The range of values for the maximal thickness of the left ventricular wall in patients with the same mutation was not significantly different from that in affected members with different mutations.

The Determination of Whether the Presence of a Particular β Cardiac Myosin Heavy-Chain Gene Mutation is Prognostic Several indexes of survival in relation to genotype (Table 2 in FIG. 6) combining data on families with identical mutations were compared to determine whether the presence of a particular β cardiac myosin heavy-chain gene mutation is prognostic. Disease-related deaths were less frequent in families with the Val606Met mutation than in families with the Arg249Gln, Arg403Gln, or Arg453Cys mutation (Table 2). Patients with the Arg249Gln mutation had a significantly longer life expectancy (Table 2) than those with the Arg403Gln mutation (P—0.027) or those with the Arg453Cys mutation (P=0.023). Survival analysis of the small families with the Gly584Arg, Glu924Lys, and Glu949Lys mutations provided little information.

Sufficient numbers of affected members were available for Kaplan-Meier product-limit survival curves to be produced for five mutations. The data for Family B and Family E were combined because the survival curve for patients with the Arg453Cys mutation involving the hybrid gene (Family B) was indistinguishable from the curve for the patients without this gene (Family E). These analyses confirmed that the Val606Met mutation was associated with longer survival than was the Arg453Cys mutation (P=0.002) or the Arg403Gln mutation (P=0.002). The Arg249Gln mutation appeared to produce an intermediate phenotype. Survival was longer among patients with this mutation than those with the Arg453Cys mutation (P=0.027) or those with the Arg403Gln mutation (P=0.015), but tended to be shorter than survival among patients with the Val606Met mutation (P=0.067). Survival among patients with the Arg453Cys mutation (with or without the hybrid gene) was similar to survival among those with the Arg403Gln mutation (P=0.79). Both mutations were associated with a particularly poor prognosis.

Results of Study

Mutations in the β cardiac myosin heavy-chain gene was identified in 12 of 25 families with FHC as shown in Table 2. Seven different missense mutations were found that are located in the head or head-rod junction region of the myosin heavy chain. No mutations were detected in he rod region. Six of the seven nucleotide substitutions altered the charge of the encoded amino acids and were particularly likely to lead to regional conformational changes in the polypeptide. The survival of affected family members, but not the extent of cardiac hypertrophy or symptoms, appears to be influenced by the particular mutation.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A non-invasive method for diagnosing hypertrophic cardiomyopathy. comprising:
    obtaining a blood sample from a subject being tested for hypertrophic cardiomyopathy;
    detecting the presence or absence of a familial hypertrophic cardiomyopathy-associated mutation in β cardiac myosin heavy-chain RNA from cells within the blood sample; and
    diagnosing the subject for hypertrophic cardiomyopathy using the presence or absence of a hypertrophic cardiomyopathy-associated mutation in the RNA as an indicator of the disease.

2. The method of claim 1 wherein the presence or absence of a hypertrophic cardiomyopathy-associated mutation in the RNA is detected by preparing β cardiac myosin heavy-chain cDNA from the RNA forming β cardiac myosin heavy-chain DNA and detecting mutations in the cDNA as being indicative of mutations in the RNA.

3. The method of claim 2 further comprising amplifying the β cardiac myosin heavy-chain cDNA prior to detecting a hypertrophic cardiomyopathy-associated mutations in the cDNA.

4. The method of claim 1 wherein the hypertrophic cardiomyopathy is familial hypertrophic cardiomyopathy.

5. The method of claim 1 wherein the hypertrophic cardiomyopathy is sporadic hypertrophic cardiomyopathy.

* * * * *